United States Patent [19]

Okabayashi et al.

[11] Patent Number: 5,051,453
[45] Date of Patent: Sep. 24, 1991

[54] CEMENT COMPOSITION

[75] Inventors: Minahiro Okabayashi, Yokohama; Hideki Ohno, Fujisawa; Koshi Kusumoto, Kamakura, all of Japan

[73] Assignee: Tokuyama Soda Kabushiki Kaisha, Yamaguchi, Japan

[21] Appl. No.: 304,200

[22] Filed: Jan. 31, 1989

[30] Foreign Application Priority Data

Feb. 8, 1988 [JP] Japan ................................ 63-25744

[51] Int. Cl.$^5$ ................................................ C08L 7/00
[52] U.S. Cl. ....................................... 523/116; 501/40; 106/35; 524/2; 524/5; 524/492
[58] Field of Search ................ 524/2, 492, 5; 106/35; 501/40; 523/116

[56] References Cited

U.S. PATENT DOCUMENTS 4,376,835  3/1983  Schmitt et al. ...................... 523/116
4,758,612  7/1988  Wilson et al. ...................... 523/116
4,814,362  3/1989  Billington et al. .................. 523/117

Primary Examiner—Paul R. Michl
Assistant Examiner—Yong S. Lee
Attorney, Agent, or Firm—Sherman and Shalloway

[57] ABSTRACT

Disclosed in a cement composition comprising an unsaturated carboxylic acid polymer and an alkaline earth metal aluminofluorosilicate glass, wherein the alkaline earth metal aluminofluorosilicate glass comprises (a) 50 to 95% by weight of coarse particles having a spherical shape and an F/Si ratio of at least 0.1 but lower than 0.6 and having a particle size larger than 3 μm but not larger than 50 μm and (b) 5 to 50% by weight of fine particles having an F/Si ratio of 0.6 to 5 and a particle size of up to 3 μm.

This cement composition gives a cured body having a good surface gloss and a high strength, and this cement composition has a good flowability and a good workability. Accordingly, the cement composition is valuable as a dental cement composition.

15 Claims, No Drawings

CEMENT COMPOSITION

BACKGROUND OF THE INVENTION (1) Field of the Invention

The present invention relates to a novel cement composition comprising an unsaturated carboxylic acid polymer and a specific alkaline earth metal aluminofluorosilicate glass.

(2) Description of the Related Art

A cement composition comprising an unsaturated carboxylic acid polymer and an alkaline earth metal aluminofluorosilicate glass as main constituents is known as an ionomer cement in which an acid-base reaction caused when both the components are mixed is utilized. This cement composition is cured in a short period in the wet state, and a cured body is obtained having a practically sufficient strength. Therefore, use of this cement composition in various application fields has been examined. Especially, when this cement composition is used as a dental cement, the composition has a high affinity with a hard texture of tooth, and the composition is substantially harmless to a living body. Accordingly, the cement composition is practically used widely as a cavity lining cement for protecting the dental pulp or a filling cement for remedy of a cuneiform defect at a collum dentis.

The alkaline earth metal aluminofluorosilicate glass is generally obtained by pulverizing a bulky glass synthesized by the melting process and is composed of pulverized particles having a particle size of several submicrons to scores of microns (see the published specification of British Patent No. 1,316,129).

When this cement composition is used as a filling cement, since the composition contains large particles as mentioned above, the gloss on the surface of the cured body is poor and an unpleasant touch is given to the tongue of a patient.

In general, a cured body of a cement composition is required to have a strength sufficient to resist an occlusion pressure. Therefore, in the above-mentioned cement composition, in order to improve the strength of the cured body, there is adopted a method in which the content of the alkaline earth metal aluminofluorosilicate glass in the composition is increased.

However, if this method is adopted, the flowability of the conventional cement composition comprising pulverized particles is drastically degraded and the workability is reduced. Therefore, a cement composition providing a cured body having a sufficient strength has not been developed as yet.

When the above-mentioned dental cement composition is used as a dental adhesive material for bonding a metal to tooth, in order to obtain a high adhesion strength, the thickness of the bonding film of the cement composition should be reduced, and therefore, a higher flowability is required than the flowability required when the cement composition is used as a filling cement.

However, in order to obtain a sufficient flowability by using the conventional cement composition comprising pulverized glass particles, it is necessary to reduce the content of the alkaline earth metal aluminofluorosilicate glass in the cement composition, and, therefore, drastic degradation of the strength of the cured body cannot be avoided.

As means for improving the flowability alone, there can be considered a method in which a filler having a spherical shape is used (see the published specification of British Patent No. 1,599,753). However, even if a known spherical filler is used, a cement composition providing a cured body having a sufficient strength cannot be obtained.

SUMMARY OF THE INVENTION

It is therefore a primary object of the present invention to provide a cement composition giving a cured body having an excellent surface gloss.

Another object of the present invention is to provide a cement composition as a dental adhesive, which has a sufficient flowability required for the dental adhesive and gives a cured body having a sufficient strength.

Still another object of the present invention is to provide a dental cement composition having a good flowability suitable for the operation and giving a cured body having an excellent surface gloss and a high strength.

In accordance with the present invention, there objects are attained by using as the inorganic filler component a cement composition comprising at least two kinds of alkaline earth metal aluminofluorosilicate glasses having specific properties.

More specifically, in accordance with the present invention, there is provided a cement composition comprising an unsaturated carboxylic acid polymer and an alkaline earth metal aluminofluorosilicate glass, wherein the alkaline earth metal aluminofluorosilicate glass comprises (a) 50 to 95% by weight of coarse particles having a spherical shape and an F/Si ratio of at least 0.1 but lower than 0.6 and having a particle size larger than 3 $\mu$m but not larger than 50 $\mu$m and (b) 5 to 50% by weight of fine particles having an F/Si ratio of from 0.6 to 5 and a particle size of up to 3 $\mu$m.

By the term "F/Si ratio" used in the instant specification and claims is meant the ratio of the number of fluorine atoms to the number of silicon atoms.

DETAILED DESCRIPTION OF THE PREFERRED EMBODIMENTS

The first component of the cement composition of the present invention is an unsaturated carboxylic acid polymer. By the unsaturated carboxylic acid polymer is meant not only a homopolymer of an unsaturated carboxylic acid monomer but also a copolymer comprising an unsaturated carboxylic acid monomer as one component.

The unsaturated carboxylic acid polymer should have such a property that when the unsaturated carboxylic acid polymer is kneaded with an alkaline earth metal aluminofluorosilicate glass described below in the presence of water, the unsaturated carboxylic acid polymer is crosslinked and cured by a crosslinking ion dissolved out from the glass, such as a calcium or aluminum ion. Therefore, a water-soluble polymer is used as the unsaturated carboxylic acid polymer. Such unsaturated carboxylic acid polymers and processes for the preparation thereof are known in the field of dental surgery. In the present invention, these known unsaturated carboxylic acid polymers can be used without any limitation. A typical instances, there can be mentioned homopolymers of an unsaturated carboxylic acid such as acrylic acid, methacrylic acid, itaconic acid, maleic acid, glutaconic acid, aconitic acid, citraconic acid, mesaconic acid, tiglic acid, fumaric acid, allylmalonic acid, crotonic acid or vinylacetic acid and copolymers comprising an unsaturated carboxylic acid as mentioned above as one component. A copolymer comprising at least 5 mole % of the unsaturated carboxylic acid is preferably used. As examples of the preferred comonomer, there can be mentioned acrylic acid esters such as ethyl acrylate, propyl acrylate and butyl acrylate, methacrylic acid esters such as methyl methacrylate, ethyl methacrylate, propyl methacrylate, butyl methacrylate, hydroxyethyl methacrylate, diethylene glycol monomethacrylate and triethylene glycol monomethacrylate, and styrene. A copolymer of acrylic acid with other unsaturated carboxylic acid, having an acrylic acid content of 5 to 95 mole %, is especially preferred.

The molecular weight of the unsaturated carboxylic acid polymer is not particularly critical, but it is generally preferred that the weight average molecular weight of the unsaturated carboxylic acid polymer is 5,000 to 500,000.

The amount used of the unsaturated carboxylic acid polymer differs according to the properties required for the cement composition of the present invention and cannot be simply defined in the present invention, but good results are generally obtained when the unsaturated carboxylic acid polymer is used in an amount of 10 to 200% by weight, preferably 20 to 100% by weight, based on the alkaline earth metal aluminofluorosilicate glass, that is, the sum of coarse particles and fine particles of the alkaline earth metal aluminofluorosilicate glass.

The other component constituting the cement composition of the present invention is an alkaline earth metal aluminofluorosilicate glass. This glass per se is known and used for a dental cement, for example, a glass-ionomer cement. Accordingly, the process for the preparation of this glass is not particularly critical, and a glass prepared according to a known process can be used. For example, the glass can be obtained by the so-called melting process in which a mixture of alumina, silica, aluminum fluoride, aluminum phosphate and an alkaline earth metal fluoride containing co-present boric acid or cryolite (aluminum sodium fluride) is molten. In general, the obtained alkaline earth metal aluminofluorosilicate glass comprises 10 to 33% by weight of a silicon ion, 4 to 30% by weight of an aluminum ion, 5 to 35% by weight of an alkaline earth metal ion, up to 10% by weight of an alkali metal ion, 0.2 to 16% by weight of a phosphorus ion and 2 to 40% by weight of a fluorine ion, with the balance being oxygen. Preferably, the glass comprises 12 to 25% by weight of a silicon ion, 7 to 20% by weight of an aluminum ion, 8 to 24% by weight of an alkaline earth metal ion, up to 7% by weight of an alkali metal ion, 0.5 to 10% by weight of a phosphorus ion and 4 to 40% by weight of a fluorine ion, with the balance being oxygen.

Most typically, the alkaline earth metal is calcium, and a part or all of calcium is preferably substituted by magnesium, strontium or barium. Sometimes, strontium is preferably used because strontium gives a cured body having a sufficient strength and an X-ray-impermeability.

Sodium is most popular as the alkali metal, but a part or all of sodium can be substituted by lithium or potassium. If necessary, a part of aluminum can be substituted by titanium, yttrium, zirconium, hafnium, tantalum or lanthanum. Moreover, a part of the glass component can be replaced by other component, so far as the physical properties of the obtained cement composition are not substantially degraded.

In the present invention, at least two kinds of alkaline earth metal aluminofluorosilicate glasses should be used. Spherical coarse particles having an F/Si ratio of at least 0.1 but lower than 0.6, preferably an F/Si ratio of from 0.1 to 0.5, and a particle size larger than 3 μm but not larger than 50 μm, preferably a particle size larger than 3 μm but not larger than 30 μm, are used as one alkaline earth metal aluminofluorosilicate glass. The coarse particles exert an important role of increasing the content of the alkaline earth metal aluminofluorosilicate glass in the cement composition and increasing the strength of a cured body of the cement composition. Since the coarse particles have a spherical shape, a preferred flowability is given to the cement composition and the workability is improved. The technique of preparing a spherical alkaline earth metal aluminofluorosilicate glass is a very peculiar technique, and according to the technique available at the present, it is difficult to obtain spherical particles having a high F/Si ratio. The spherical alkaline earth metal aluminofluorosilicate glass used in the present invention is generally prepared by pulverizing a glass obtained by the above-mentioned melting process to obtain pulverized particles, collecting pulverized particles having a required size by sieving and passing the collected pulverized particles through a flame. The so-obtained glass is a very special product, and this glass is not commercially available at the present.

Industrial production of the spherical alkaline earth metal aluminofluorosilicate glass having a high F/Si ratio is difficult, and the highest F/Si ratio attainable by the technique available at the present is about 0.6. If the F/Si ratio is extremely low, for example, lower than 0.1, the strength of a cured body of the cement composition is not satisfactory in many cases. Therefore, the F/Si ratio in the coarse particles of the alkaline earth metal aluminofluorosilicate glass used in the present invention is at least 0.1 but lower than 0.6, preferably at least 0.1 but lower than 0.5.

The alkaline earth metal aluminofluorosilicate glass used in the present invention should have a spherical shape, but it is not absolutely necessary that the shape should be a true sphere. In general, the glass in which the content of particles having a circularity, defined hereinafter, of 0.9 to 1.0 is at least 90% by weight, especially at least 95% by weight, is preferably used. The alkaline earth metal aluminofluorosilicate pulverized particles having a particle size larger than 3 μm but not larger than 50 μm, can be added to the spherical coarse particles. The amount of the pulverized particles is preferably less than 2% by weight of the coarse particles.

The above-mentioned spherical coarse particles of the alkaline earth metal aluminofluorosilicate glass give a preferred flowability to the cement composition and the workability is highly improved. However, it was found that if only such spherical coarse particles alone are incorporated, the strength of the cement composition is still insufficient to some extent.

In the present invention, in order to overcome this disadvantage, in addition to the above-mentioned coarse particles, fine particles of the alkaline earth metal aluminofluorosilicate glass having an F/Si ratio of 0.6 to 5 and a particle size of up to 3 μm are incorporated. In order to impart a sufficient strength to a cured body of the cement composition, the F/Si ratio in the fine particles should be relatively high and in the range of from 0.6 to 5. To our surprise, it was found that when the fine particles are used in combination with the coarse particles having the above-mentioned properties, the F/Si ratio of the fine particles has important influences on the strength of a cured body of the cement composition. However, so far as the fine particles are used in combination with the coarse particles having the above-mentioned properties, the shape of the fine particles has no significant influneces on the physical properties of the cement composition. Therefore, the fine particles may be spherical particles, pulverized particles or mixtures thereof. Since the fine particles having a relatively high F/Si ratio should be used, use of pulverized particles obtained by pulverizing the alkaline earth metal aluminofluorosilicate glass obtained by the above-mentioned melting process and collecting particles having a required particle size is economically advantageous because the manufaturing cost is smallest.

As pointed out hereinbefore, in order to improve the strength of a cured body of the cement composition, it is indispensable that the particle size of the fine particles should be up to 3 μm. It has not been completely elucidated what function is exerted by the fine particles. However, if it is taken into consideration that if the fine particles are not incorporated, a long setting time is necessary and the strength of the cured body is insufficient, it is construed that since the fine particles have a large surface area, the setting time can be adjusted and a high degree of crosslinking can be attained. Furthermore, it is construed that synergistic effects can be attained by the specific particle size and F/Si ratio, and high strength, high workability and excellent surface gloss can be effectively realized in the present invention that cannot be attained in a cured body of the conventional ionomer cement.

In the cement composition of the present invention, the mixing ratio between coarse particles and fine particles of the alkaline earth metal aluminofluorosilicate glass differs according to the properties required for the cement composition and this mixing ratio cannot be simply defined. However, it is generally preferred that the glass should comprise 50 to 95% by weight of the coarse particles and 5 to 50% by weight of the fine particles.

In the present invention, it is sufficient if at least two kinds of the above-mentioned alkaline earth metal aluminofluorosilicate glass particles are used. Furthermore, a known inorganic oxide such as quartz, silica, strontium oxide, zirconium oxide or lanthanum oxide can be incorporated in addition to the coarse and fine particles, so far as the physical properties of the cement composition are not substantially degraded.

The amount added of the alkaline earth metal aluminofluorosilicate glass used in the cement composition of the present invention differs according to the physical properties required for the cement composition, but in general, it is sufficient if the glass is incorporated in such an amount that the amount of the unsaturated carboxylic acid polymer is 10 to 200% by weight based on the glass, as pointed out hereinbefore.

The storage state of the cement composition is not particularly critical, since the components there of are mixed in the above-mentioned amounts when the cement composition is actually used. As typical examples of the storage state, there can be mentioned an embodiment in which the alkaline earth metal alumino-fluorosilicate glass and an aqueous solution of the unsaturated carboxylic acid polymer are stored in different packs, and also an embodiment in which the glass and the unsaturated carboxylic acid polymer are mixed in the absence of water.

The former type of composition is a two-pack type where the unsaturated carboxylic acid polymer and the alkaline earth metal aluminofluorosilicate glass are stored in different packs, and they are removed from the packs and mixed when the cement composition is cured. The latter type of composition is a two-pack type where the unsaturated carboxylic acid polymer and the alkaline earth metal aluminofluorosilicate glass are stored in the substantially dry anhydrous state in one pack and they are mixed and kneaded with water in another pack when the cement composition is cured.

In the embodiment where a pack of an aqueous solution of the unsaturated carboxylic acid polymer is used, it is preferred that the concentration of the polymer in the aqueous solution be 30 to 70% by weight, especially 40 to 60% by weight.

According to need, water and other additives such as acids, e.g., tartaric acid, citric acid, malic acid and phosphoric acid, pigments and fluorine compounds, e.g., sodium fluoride and potassium fluorotitanate, can be appropriately added to the cement composition of the present invention, so far as bad influences are not substantially imposed on the reaction between the unsaturated carboxylic acid polymer and the glass.

Since mixing is possible at a higher powder/liquid ratio in case of the cement composition of the present invention than in the case of conventional cement compositions, the obtained cured body has a higher mechanical strength. Moreover, even if the cement composition of the present invention is used at a high powder/liquid ratio, by the mutual action of the coarse and fine particles, curing is accomplished in an appropriate time, and the obtained cured body has an excellent surface gloss. Accordingly, if the cement composition is clinically used as a dental filling material, it does not give the unpleasant sandy touch given to the tongue of a patient in the case of a conventional cement composition.

When the cement composition of the present invention is used as a dental luting cement, a high flowability is attained at the mixing step and a cured body having a high strength can be obtained.

The present invention will now be described in detail with reference to the following examples that by no means limit the scope of the invention. Incidentally, the properties of materials shown in the text and examples were determined according to the following methods.

(1) Particle Size and Average Particle Size

The obtained particles were dispersed in water and the particle size was measured by a particle size distribution meter (supplied by Malvern). The measurement principle was that of the measurement of the scattered diffraction pattern by laser beams.

(2) Specific Surface Area

The specific surface area was measured by a quick surface area-measuring apparatus (Model SA-1000 supplied by Shibata Kagaku Kiki Kogyo). The measurement principle was that of the BET method.

(3) Circularity of Particles

A scanning electron microscope of the sample powder was taken, and with respect to n of particles observed in the unit visual field of the photo, from the length ($L_i$) of the profile and the length ($M_i$) of the circumference of the circle having the same area as the area of the particle on the. The circularity was calculated according to the following formula:

$$\text{Circularity} = \left( \sum_{i=1}^{n} Mi/Li \right)/n$$

The closer to 1.00 is the value of the circularity, the closer to a true sphere is the particle shape.

(4) Composition of Glass

The composition of the glass was determined by qualitative and quantitative analysis using a fluorescent X-ray analysis apparatus (supplied by Rigaku Denki).

(5) Structure of Glass

The X-ray diffraction of the sample powder was determined by an X-ray diffractometrical apparatus (supplied by Nippon Denshi), and the crystal structure (form) of the alkaline earth metal aluminofluorosilicate glass was examined.

(6) Maximum Powder/Liquid Ratio

The glass powder and an aqueous solution containing the unsaturated carboxylic acid polymer at a concentration of 50% by weight were kneaded at room temperature (23° C.) at various mixing ratios between the glass and the aqueous solution of the unsaturated carboxylic acid polymer, and the maximum mixing weight of the glass powder that could maintain a flowability after 45 seconds from the start of mixing was determined. The maximum powder/liquid ratio (Wp/Wl) was calculated from the weight (Wl) of the aqueous solution of the unsaturated carboxylic acid polymer to the above-mentioned maximum mixing weight (Wp) of the glass powder.

(7) Setting Time of Cement

The setting time was determined according to the coagulation test for a dental zinc phosphate cement, specified in JIS T-6602.

More specifically, a Teflon mold having an inner size of 10 mm×10 mm×2 mm was filled with a cement which had been kneaded for 45 seconds, and the surface of the charged cement was flattened. When 2 minutes had passed from the start of the kneading, the cement was transfered into a thermostat tank maintained at a temperature of 37° C. and a relative humidity of 100%. Then, a Gilmore needle having a weight of 560 g (the sectional area of the needle was 1 mm$^2$) was gently dropped on the surface of the test piece. The time elapsed from the start of the kneading to the point at which no dropping mark was formed on the surface by the needle was designated as the setting time.

(8) Compression Strength

The compression strength was determined according to the breaking strength test for a zin phosphate cement, specified in JIS T-6602.

More specifically, a cement which had been kneaded for 45 seconds, was charged in a columnar mold having a height of 12 mm and a diameter of 6 mm, and was held for 1 hour in a thermostat tank maintained at a temperature of 37° C. and a relative humidity of 100%. The cured body was taken out from the mold, and this test piece was held in distilled water at 37° C. for 23 hours and compressed at a cross head speed of 1 mm/min by using a Tensilon tester (supplied by Toyo-Boldwin) until the test piece was broken. The breaking strength was designated as the compression strength (kg/cm$^2$).

(9) Surface Roughness

A Teflon mold having an inner size of 10 mm×10 mm×2 mm was filled with a cement obtained by mixing the glass and an aqueous solution of the unsaturated carboxylic acid polymer at the above-mentioned maximum powder/liquid ratio for 45 seconds, and the surface of the cement was covered with a polypropylene sheet and a glass plate was compressed on the polypropylene sheet. The assembly was held in a thermostat tank maintained at a temperature of 37° C. and a relative humidity of 100% for 1 hour. The cured body was taken out from the mold. This test piece was kept in distilled water at 37° C. for 23 hours. The test piece was polished for 5 seconds by an abrasive paper of #1500, and furthermore, the surface was violently polished for 1 minute by a filter paper.

The surface roughness of the so-obtained test piece was determined according to the 10-point average roughness (RZ) method of JIS 0601-1982 by using a surface roughness and shape measuring apparatus (supplied by Tokyo Seimitsu).

(10) Consistency

The glass was kneaded with an aqueous solution of the unsaturated carboxylic acid polymer at a predetermined powder/liquid ratio for 45 seconds, and the mixture was filled in a syringe having a capacity of 1 ml. Then, 1 ml of the mixture was placed on a glass plate having a size of 50 mm×50 mm×3 mm and another glass plate having a size of 40 mm×40 mm×3 mm was quietly placed on the mixture. When 2 minutes had passed from the start of the mixing, a weight of 2.5 kg was placed on the upper glass plate and this state was maintained for 8 minutes. The weight was removed, and the maximum diameter and minimum diameter of the cured body were measured and the mean value was calculated as the consistency (unit: mm).

Incidentally, in Examples 1 through 8 and 11 and Comparative Examples 1 through 5, in order to examine the aptitude for a filling cement composition, the maximum powder/liquid ratio was adopted for forming a cured body having a high strength.

In Examples 9 and 10 and Comparative Examples 6 through 10, in order to examine the aptitude for an adhesive cement composition, a relatively low powder/liquid ratio was adopted for obtaining a high flowability.

EXAMPLE 1

A mixed powder obtained by mixing a powder comprising 120 g of silica (Crystallite AA supplied by Tatsumori), 42 g of aluminum hydroxide (supplied by Wako Junyaku), 28 g of artificial cryolite (supplied by Morita Kagaku), 78 g of aluminum phosphate (supplied by Taihei Kagaku Sangyo), 24 g of aluminum fluoride (supplied by Wako Junyaku) and 56 g of calcium fluoride (supplied by Wako Junyaku) in a ball mill for 3 hours was charged in a platinum crucible and heat-molten at 1400° C. for 30 minutes. Subsequently, the melt was transferred to a water bath and rapidly cooled. The obtained glass was pulverized in a vibrating ball mill. The powder obtained by the pulverization was passed through a 400-mesh nylon sieve, and 150 g of the powder which had passed through the sieve was dispersed in 1 liter of methanol. The particles which were sedimented within 30 seconds were removed, and the remaining particles were divided into particles which were sedimented within 1 hour (particles A) and particles which were not sedimented (particles R).

The particles (A) were supplied at a rate of 20 g/min together with hydrogen (2.3 Nm³/hr) and oxygen (0.90 Nm³/hr) into a combustion chamber provided with a multi-pipe burner, and were dispersed and fused in a flame. The particles A were fused in a moment in the flame, and after the passage through the flame, the melt was cooled and solidified. The particles were collected by a cyclone. Then, 10 g of the so-obtained powder was kneaded with 0.4 g of ammonium fluoride and a small amount of water, dried at 100° C. for 3 hours and heated at 600° C. for 1 hour to obtain spherical coarse particles (particles C).

The so-obtained particles C had an F/Si ratio of 0.32, a circularity of 1.00, a particle size in the range of from 3.7 to 18.1 μm, an average particle size of 7.8 μm and a specific surface area of 1.0 m²/g, and the particles C were amorphous.

The particles B had an F/Si ratio of 0.65, a particle size in the range of from 0.1 to 2.7 μm, an average particle size of 0.9 μm and a specific surface area of 6.3 m²/g, and the particles B were amorphous.

A cement was prepared from a powder comprising the particles C and the particles B at a mixing ratio of 60/40 and an aqueous solution containing 50% by weight of a copolymer comprising 90 mole % of acrylic acid and 10 mole % of maleic acid (molecular weight=16,000) and 7.5% by weight of tartaric acid (hereinafter referred to as "AM polymer aqueous solution"). This cement was characterized by a maximum powder/liquid ratio of 2.5, a setting time of 4 minutes and 15 seconds, a compression strength of 1870 kg/cm² and a surface roughness of 0.47 μm.

EXAMPLES 2 through 8 and Comparative Examples 1 and 2

Cements differing in the mixing ratio between coarse and fine particles were prepared by using the particles C and B described in Example 1 and an aqueous solution of an unsaturated carboxylic acid polymer (AM polymer aqueous solution), and the physical properties were examined in the same manner as described in Example 1. The obtained results are shown in Table 1.

COMPARATIVE EXAMPLE 3

A glass prepared in the same manner as described in Example 1 was pulverized by a vibrating ball mill and passed through a 400-mesh nylon sieve. Then, 150 g of particles which had passed through the sieve were dispersed in 1 liter of methanol, and the particles were divided into particles which were sedimented within 5 minutes and particles which were not sedimented within 5 minutes (particles D).

From the results of the analysis, it was found that the particles D had an F/Si ratio of 6.5, a particle size in the range of from 0.1 to 5.6 μm, an average particle size of 2.3 μm and a specific surface area of 4.1 m²/g and the particles D were amorphous.

A cement was prepared from a mixed powder comprising the particles C used in Example 1 and the particles D at a weight ratio of 60/40 and the AM polymer aqueous solution. The cement was characterized by a maximum powder/liquid ratio of 2.6, a setting time of 4 minutes and 50 seconds, a compression strength of 1750 kg/cm² and a surface roughness of 0.79 μm.

COMPARATIVE EXAMPLE 4

A glass prepared in the same manner as described in Example 1 was pulverized by a vibrating ball mill and passed through a 150-mesh nylon sieve. Then, 150 g of particles which had passed through the sieve were dispersed in 1 liter of methanol, and the particles were divided into particles which were sedimented within 1 hour (particles E) and particles which were not sedimented within 1 hour.

Particles (particles F) obtained by sphering the particles E in the same manner as described in Example 1 had an F/Si ratio of 0.40, a circularity of 0.98, a particle size in the range of from 3.6 to 68.5 μm, an average particle size of 16.1 μm and a specific surface area of 0.6 m²/g, and the particles F were amorphous.

A cement was prepared from a mixed powder comprising the particles F and the particles B at a weight ratio of 60/40 and the AM polymer aqueous solution. The cement was characterized by a maximum powder/liquid ratio of 2.8, a setting time of 4 minutes and 30 seconds, a compression strength of 1740 kg/cm² and a surface roughness of 0.86 μm.

COMPARATIVE EXAMPLE 5

A cement was prepared from a mixed powder comprising the pulverized particles A obtained in Example 1 (F/Si ratio=0.65, particles size=3.3−18.1 μm, average particle size=6.6 μm, specific surface area=1.3 m²/g, amorphous) and the particles B obtained in Example 1 at a mixing weight ratio of 60/40 and the AM polymer aqueous solution. The cement was characterized by a maximum powder/liquid ratio of 2.0, a setting time of 4 minutes and 20 seconds, a compression strength of 1800 kg/cm² and a surface roughness of 1.64 μm.

The results obtained in Examples 1 through 8 and Comparative Examples 1 through 5 are summarized in Table 1.

TABLE 1

| Example No. | Coarse Particles | | | | Fine Particles | | | | Coarse Particles/ Fine Particles Weight Ratio |
|---|---|---|---|---|---|---|---|---|---|
| | name | F/Si | particle size (μm) | shape | name | F/Si | particle size (μm) | shape | |
| 1 | C | 0.32 | 3.7–18.1 | spherical | B | 0.65 | 0.1–2.7 | pulverized | 60/40 |
| 2 | C | 0.32 | 3.7–18.1 | " | B | 0.65 | 0.1–2.7 | " | 80/20 |
| 3 | C | 0.32 | 3.7–18.1 | " | B | 0.65 | 0.1–2.7 | " | 70/30 |
| 4 | C | 0.32 | 3.7–18.1 | " | B | 0.65 | 0.1–2.7 | " | 58/42 |
| 5 | C | 0.32 | 3.7–18.1 | " | B | 0.65 | 0.1–2.7 | " | 54/44 |
| 6 | C | 0.32 | 3.7–18.1 | " | B | 0.65 | 0.1–2.7 | " | 54/46 |
| 7 | C | 0.32 | 3.7–18.1 | " | B | 0.65 | 0.1–2.7 | " | 52/48 |
| 8 | C | 0.32 | 3.7–18.1 | " | B | 0.65 | 0.1–2.7 | " | 50/50 |
| C. Ex. 1 | C | 0.32 | 3.7–18.1 | " | B | 0.65 | 0.1–2.7 | " | 97/3 |
| C. Ex. 2 | C | 0.32 | 3.7–18.1 | " | B | 0.65 | 0.1–3.7 | " | 30/70 |
| C. Ex. 3 | C | 0.32 | 3.7–18.1 | " | B | 0.65 | 0.1–5.6 | " | 60/40 |

TABLE 1-continued

| | | | | | | | | | |
|---|---|---|---|---|---|---|---|---|---|
| C. Ex. 4 | F | 0.40 | 3.6–68.5 | " | B | 0.65 | 0.1–2.7 | " | 60/40 |
| C. Ex. 5 | A | 0.65 | 3.3–18.1 | pulverized | B | 0.65 | 0.1–2.7 | " | 60/40 |

| Example No. | Maximum Powder/ Liquid Weight Ratio | Setting Time (minutes, second) | Compression Strength (Kg/cm²) | Surface Roughness (μm) |
|---|---|---|---|---|
| 1 | 2.5 | 4'15" | 1870 | 0.47 |
| 2 | 3.0 | 6'30" | 1800 | 0.52 |
| 3 | 2.7 | 5'10" | 1870 | 0.48 |
| 4 | 2.4 | 4'50" | 1880 | 0.46 |
| 5 | 2.3 | 4'30" | 1860 | 0.45 |
| 6 | 2.3 | 4'20" | 1850 | 0.45 |
| 7 | 2.2 | 4'10" | 1840 | 0.44 |
| 8 | 2.2 | 4'00" | 1820 | 0.40 |
| C. Ex. 1 | 3.1 | 10'30" | 1380 | 0.55 |
| C. Ex. 2 | 1.7 | 2'10" | 1430 | 0.35 |
| C. Ex. 3 | 2.6 | 4'50" | 1750 | 0.79 |
| C. Ex. 4 | 2.8 | 4'30" | 1740 | 0.86 |
| C. Ex. 5 | 2.0 | 4'20" | 1800 | 1.64 |

C. Ex.: Comparative Example No.

EXAMPLE 9

A powder obtained by mixing 120 g of silica (Crystallite AA supplied by Tatsumori), 81 g of aluminum hydroxide (supplied by Wako Junyaku), 44 g of aluminum phosphate (supplied by Taihei Kagaku Sangyo), 50 g of aluminum fluoride (supplied by Wako Junyaku), 44 g of calcium fluoride (supplied by Wako Junyaku) and 13 g of sodium fluoride (supplied by Wako Junyaku) in a ball mill for 3 hours was charged in a platinum crucible and heat-molten at 1300° C. for 30 minutes. Subsequently, the melt was rapidly cooled in a water bath, and in the same manner as described in Example 1, the obtained glass was pulverized and classified to obtain coarse particles (particles G) and fine particles (particles H).

Then, in the same manner as described in Example 1, the particles G were sphered to obtain spherical particles J.

From the results of the analysis, it was found that the particles J had an F/Si ratio of 0.44, a circularity of 1.00, a particle size in the range of 4.1 to 16.3 μm, an average particle size of 6.3 μm and a specific surface area of 1.2 m²/g and the particles J were amorphous. The particles H had an F/Si ratio of 0.80, a particle size in the range of 0.1 to 2.7 μm, an average particle size of 1.1 μm and a specific surface area of 5.4 m²/g and the particles H were amorphous.

A cement was prepared from a mixed powder comprising the particles J ahd H at a weight ratio of 90/10 and the AM polymer aqueous solution. In order to examine the aptitude for an adhesive cement, the cement was kneaded at a powder/liquid of 1.9. It was found that the consistency was 31 mm, the setting time was 5 minutes and the compression strength was 1340 kg/cm².

In the following examples and comparative examples, the aptitute for an adhesive cement was examined.

EXAMPLE 10

A cement was prepared from a mixed powder comprising the particles J ahd H obtained in Example 9 at a mixing weight ratio of 80/20 and the AM polymer aqueous solution. When the cement was kneaded at a powder/liquid ratio of 1.8, the consistency was 30 mm, the setting time was 4 minutes and 20 seconds and the compression strength was 1410 kg/cm².

COMPARATIVE EXAMPLE 6

A cement was prepared from a mixed powder comprising the particles J and H obtained in Example 9 at a mixing weight ratio of 40/60 and the AM polymer aqueous solution. When the cement was kneaded at a powder/liquid ratio of 1.8, the consistency was 25 mm, the setting time was 2 minutes and 10 seconds and the compression strength was 1380 kg/cm².

COMPARATIVE EXAMPLE 7

A cement was prepared from a mixed powder comprising the pulverized particles G obtained in Example 9 (F/Si ratio=0.8, particle size=4.1–18.1 μm, average particle size=7.1 μm, specific surface area=1.6 m²/g, amorphous) and the particles H obtained in Example 9 at a mixing weight ratio of 90/10 and the AM polymer aqueous solution. When the cement was kneaded at a powder/liquid ratio of 1.8, the consistency was 24 mm, the setting time was 4 minutes and 40 seconds and the compression strength was 1330 kg/cm².

COMPARATIVE EXAMPLE 8

When the cement prepared in Comparative Example 6 was kneaded at a powder/liquid ratio of 1.5, the consistency was 30 mm, the setting time was 6 minutes and 10 seconds and the compression strength was 930 kg/cm².

COMPARATIVE EXAMPLE 9

A powder obtained by mixing 120 g of silica (Crystallite AA supplied by Tatsumori), 127 g of aluminum hydroxide (supplied by Wako Junyaku), 44 g of aluminum phosphate (supplied by Taihei Kagaku Sangyo), 56 g of calcium carbonate (supplied by Nippon Sekkai) and 26 g of sodium carbonate (supplied by Wako Junyaku) in a ball mill for 3 hours was charged in a platinum crucible and heat-molten at 1400° C. for 30 minutes. Subsequently, the melt was rapidly cooled in a water bath, and in the same manner as described in Example 1, the obtained glass was pulverized and classified and the obtained coarse particles were sphered to obtain spherical particles K.

From the results of the analysis, it was found that the particles K had an F/Si ratio of 0, a circularity of 1.00, a particle size in the range of 3.3 to 15.6 μm, an average particle size of 6.4 μm and a specific surface area of 1.1 m²/g and the particles K were amorphous.

A cement was prepared from a mixed powder comprising the particles K and the particles H obtained in Example 9 at a mixing weight ratio of 80/20 and the AM polymer aqueous solution. When the cement was kneaded at a powder/liquid ratio of 1.9, the consistency was 29 mm, the setting time was 6 minutes and 40 seconds and the compression strength was 1070 kg/cm$^2$.

COMPARATIVE EXAMPLE 10

A powder obtained by mixing 120 g of silica (Crystallite AA supplied by Tatsumori), 81 g of aluminum hydroxide (supplied by Wako Junyaku), 44 g of aluminum phosphate (supplied by Taihei Kagaku Sangyo), 50 g of aluminum fluoride (supplied by Wako Junyaku), 56 g of calcium carbonate (supplied by Nippon Sekkai) and 26 g of sodium carbonate (supplied by Wako Junyaku) in ball mill for 3 hours was charged in a platinum crucible and heat-molten at 1400° C. for 30 minutes. Subsequently, the melt was rapidly cooled in a water bath, and in the same manner as described in Example 1, the obtained glass was pulverized and classified and fine particles (particles L) were obtained.

From the results of the analysis, it was found that the particles L had an F/Si ratio of 0.43, a particle size in the range of 0.2 to 2.4 μm, an average particle size of 1.0 μm and a specific surface area of 5.8 m$^2$/g and the particles L were amorphous.

A cement was prepared from a mixed powder comprising the particles J obtained in Example 9 and the particles L at a mixing weight ratio of 80/20 and the AM polymer aqueous solution. When the cement was kneaded at a powder/liquid ratio of 1.9, the consistency was 30 mm, the setting time was 5 minutes and 10 seconds and the compression strength was 1120 kg/cm$^2$.

The results obtained in Examples 9 and 10 and Comparative Examples 6 through 10 are summarized in Table 2.

EXAMPLE 11

Coarse spherical particles treated with ammonium fluoride (particles M) were prepared in the same manner as described in Example 1.

From the results of the analysis, it was found that the particles M had an E/Si ratio of 0.24, a circularity of 0.98, a particle size in the range of 3.3 to 16.3 μm, an average particle size of 6.9 μm and a specific surface area of 1.0 m$^2$/g, and the particles M were amorphous.

A cement was prepared from a mixed powder comprising 62 parts by weight of the particles M and 48 parts by weight of the particles B obtained in Example 1 and an aqueous solution containing 50% by weight of a copolymer comprising 75 mole % of acrylic acid and 25 mole % of of itaconic acid (molecular weight=21,000) and 10% by weight of tataric acid (hereinafter referred to as "AI polymer solution").

The cement had a maximum powder/liquid ratio of 2.7, a setting time of 4 minutes and 20 seconds, a compression strength of 1770 kg/cm$^2$ and a surface roughness of 0.40 μm.

EXAMPLE 12

A powder obtained by mixing 120 g of silica (Crystallite AA supplied by Tatsumori), 44 g of aluminum phosphate (supplied by Taihei Kagaku Sangyo), 140 g of aluminum fluoride (supplied by Wako Junyaku), 62 g of strontium fluoride (supplied by Wako Junyaku) and 10 g of sodium fluoride (supplied by Wako Junyaku) in a ball mill for 3 hours was charged in a platinum crucible and heat-molten at 1250° C. for 30 minutes. Subsequently, the melt was rapidly cooled in a water bath, and in the same manner as described in Example 1, the glass was pulverized and classified and the coarse paticles were sphered, whereby coarse spherical particles (particles N) and fine particles (particles P) were obtained.

From the results of the analysis, it was found that the particles N had an F/Si ratio of 0.49, a circularity of 1.00, a particles size in the range of 3.7 to 18.1 μm, an average particles size of 7.9 μm and a specific surface area of 0.8 m$^2$/g and the particles N were amorphous, and that the particles P had an F/Si ratio of 1.09, a particle size in the range of 0.1 to 2.4 μm, an average particle size of 1.1 μm and a specific surface area of 5.6 m$^2$/g and the particles P were amorphous.

A cement composition was prepared from a mixed powder comprising the particles N and P at a weight ratio of 80/20 and an aqueous solution containing 50% by weight of a copolymer comprising 75 mole % of acrylic acid and 25 mole % of allylmalonic acid (molecular weight=26,000) and 6.3% by weight of tartaric acid. When the cement was kneaded at a powder/liquid

TABLE 2

| Example No. | Coarse Particles | | | | Fine Particles | | | | Coarse Particles/ Fine Particles Weight Ratio |
|---|---|---|---|---|---|---|---|---|---|
| | name | F/Si | particle size (μm) | shape | name | F/Si | particle size (μm) | shape | |
| 9 | J | 0.44 | 4.1–16.3 | spherical | H | 0.80 | 0.1–2.7 | pulverized | 90/10 |
| 10 | J | 0.44 | 4.1–16.3 | " | H | 0.80 | 0.1–2.7 | " | 80/20 |
| C. Ex. 6 | J | 0.44 | 4.1–16.3 | " | H | 0.80 | 0.1–2.7 | " | 40/60 |
| C. Ex. 7 | G | 0.80 | 4.1–18.1 | pulverized | H | 0.80 | 0.1–2.7 | " | 90/10 |
| C. Ex. 8 | G | 0.80 | 4.1–18.1 | " | H | 0.80 | 0.1–2.7 | " | 90/10 |
| C. Ex. 9 | K | 0 | 3.3–15.6 | spherical | H | 0.80 | 0.1–2.7 | " | 80/20 |
| C. Ex. 10 | J | 0.44 | 4.1–16.3 | " | L | 0.43 | 0.2–2.4 | " | 80/20 |

| Example No. | Powder/Liquid Weight Ratio | Consistency (mm) | Setting Time (minutes, seconds) | Compression Strength (kg/cm$^2$) |
|---|---|---|---|---|
| 9 | 1.9 | 31 | 5'00" | 1340 |
| 10 | 1.8 | 30 | 4'20" | 1410 |
| C. Ex. 6 | 1.8 | 25 | 2'10" | 1380 |
| C. Ex. 7 | 1.8 | 24 | 4'40" | 1330 |
| C. Ex. 8 | 1.5 | 30 | 6'10" | 930 |
| C. Ex. 9 | 1.9 | 29 | 6'40" | 1070 |
| C. Ex. 10 | 1.9 | 30 | 5'10" | 1120 |

C. Ex.: Comparative Example No.

ratio of 1.8, the consistency was 31 mm, the setting time was 3 minutes and 50 seconds and the compression strength was 1450 kg/cm$^2$.

EXAMPLE 13

To a mixed solution comprising 24 ml of 0.01N hydrochloric acid and 320 ml of methanol was added 333 g of tetraethyl silicate [Si(OC$_2$H$_5$)$_4$ supplied by Nippon Colcoat], and the mixture was refluxed at 80° C. for 2 hours. Then, 551 g of aluminum tri-sec-butoxide [Al(Q-sec-C$_4$H$_9$)$_3$ supplied by Tokyo Kasei] and 58 g of triethyl phosphate [(C$_2$H$_5$O)$_3$P=O supplied by Wako Junyaku] were added to the solution, and the mixture was further refluxed for 1 hour. The obtained solution was designated as "solution A".

To 4 liters of ethanol was added 19.2 g of granular metallic calcium (supplied by Wako Junyaku), and the mixture was refluxed at 60° C. for 2 hours, whereby calcium was reacted with ethanol to form calcium diethoxide which was dissolved in ethanol. The obtained reaction solution was designated as "solution B".

The solution A was added to the solution B, and 62 g of a methanol solution containing 28% of sodium methylate (supplied by Wako Junyaku) was added and the mixture was refluxed at 80° C. for 1 hour. Then, the liquid was cooled to room temperature. A mixed liquid of 1.2 liters of aqueous ammonia and 1.2 liters of methanol, prepared in advance, was gradually added to the so-obtained liquid with stirring. When the liquid mixture was allowed to stand at room temperature. overnight, a jelly-like gel was formed. The obtained gel was dried at 60° C. for 24 hours and heated at 800° C. for 1 hour to obtain a white powder.

The obtained white powder was charged in a polyethylene beaker, pulverized by a polypropylene rod and classified by a 250-mesh nylon sieve. The powder which had passed through the sieve was used as the glass powder.

In the same manner as described in Example 1, the glass powder was supplied at a rate of 25 g/min to a flame formed by hydrogen (2.3 Nm$^3$/hr), air (2.0 Nm$^3$/hr) and oxygen (0.75 Nm$^3$/hr) by using a multipipe burner. The particles in the starting powder were fused and cooled in the course to a cyclone, and the particles were collected in the cyclone.

From the results of the analysis, it was found that the obtained powder comprised 45.5 mole %, 31.8 mole % of aluminas, 13.6 mole % of calcium oxide, 4.5 mole % of phopsphorous pentoxide and 4.5 mole % of sodium oxide and the composition was equal to the composition calculated from the charged amounts.

Then, 10 g of the obtained powder was kneaded with 0.4 g of ammonium fluoride and an appropriate amount of water, and the mixture was dried at 100° C. for 3 hours and heated at 600° C. for 1 hour to obtain a powder Q.

The obtained powder Q had an F/Si ratio of 0.14, a circularity of 0.99, a particle size in the range of 3.3 to 18.1 µm, an average particle size of 7.5 µm and a specific surface area of 2.7 m$^2$/g and the powder Q was amorphous.

A cement was prepared from a mixed powder comprising 70 parts by weight of the powder Q and 30 parts by weight of the powder B obtained in Example 1 and the Al polymer solution used in Example 11.

The cement was characterized by a maximum powder/liquid ratio of 2.4, a setting time of 4 minutes and 40 seconds, a compression strength of 1820 kg/cm$^2$ and a surface roughness of 0.41 µm.

EXAMPLE 14

A cement composition was prepared from a mixed powder comprising the particles N and P used in Example 12 at a mixing weight ratio of 70/30 and an aqueous solution containing 50% by weight of a copolymer comprising 65 mole % of acrylic acid, 25 mole % of allylmalonic acid and 10 mole % of styrene (molecular weight=17,000) and 6.3% by weight of tartaric acid. When the cement was kneaded at a powder/liquid ratio of 1.8, the consistency was 30 mm, a setting time was 4 minutes and 20 seconds and the compression strength was 1350 kg/cm$^2$.

We claim:

1. A cement composition comprising poly(unsaturated carboxylic acid) and an alkaline earth metal aluminofluorosilicate glass, wherein the alkaline earth metal aluminofluorosilicate glass comprises (a) 50 to 95% by weight of coarse particles having a spherical shape and an F/Si ratio of at least 0.1 but lower than 0.6 and having a particle size larger than 3 µm but not larger than 50 µm and (b) 5 to 50% by weight of finely pulverized particles having an F/Si ratio of 0.6 to 5 and a particle size of up to 3 µm.

2. A cement composition as set forth in claim 1, wherein poly(unsaturated carboxylic acid) is a copolymer of acrylic acid with other unsaturated carboxylic acid.

3. A cement composition as set forth in claim 2, wherein poly(unsaturated carboxylic acid) is a copolymer containing 5 to 95 mole % of acrylic acid.

4. A cement composition as set forth in claim 1, wherein the coarse particles have an F/Si ratio of 0.1 to 0.5 and a particle size larger than 3 µm but not larger than 30 µm.

5. A cement composition as set forth in claim 1, wherein the fine particles have an F/Si ratio of 0.7 to 4.

6. A cement composition as set forth in claim 5, wherein the fine particles are those obtained by pulverizing an alkaline earth metal aluminofluorosilicate glass prepared by the melting process.

7. A cement composition as set forth in claim 1, wherein poly(unsaturated carboxylic acid) is incorporated in an amount of 10 to 200% by weight based on the alkaline earth metal aluminofluorosilicate glass.

8. A cement composition as set forth in claim 1, which is of a two-pack type where poly(unsaturated carboxylic acid) and the alkaline earth metal aluminofluorosilicate glass are stored in different packs, and they are taken out from the packs and mixed when the cement composition is cured.

9. A cement composition as set forth in claim 8, wherein poly(unsaturated carboxylic acid) is packed in the form of an aqueous solution.

10. A cement composition as set forth in claim 9, wherein the concentration of poly(unsaturated carboxylic acid) is 30 to 70% by weight.

11. A cement composition as set forth in claim 1, which is of a two-pack type where the unsaturated carboxylic acid polymer and the alkaline earth metal aluminofluorosilicate glass are stored in the substantially dry anhydrous state in one pack and they are mixed with water in another pack when the cement composition is cured.

12. A cement composition as set forth in claim 9, wherein the concentration of poly(unsaturated carboxylic acid) is 40 to 60% by weight.

13. A cement composition as set forth in claim 1, wherein the poly(unsaturated carboxylic acid) has an average molecular wt. of from 5,000 to 500,000.

14. A cement composition as set forth in claim 1, wherein poly(unsaturated carboxylic acid) is incorporated in an amount of 20-100% by weight based on the alkaline earth metal aluminofluorosilicate glass.

15. A cement composition as set forth in claim 1, wherein at least 90% of the glass has a circularity of 0.9 to 1.0.

* * * * *